United States Patent
Kontiola et al.

(10) Patent No.: US 11,659,994 B2
(45) Date of Patent: May 30, 2023

(54) METHOD AND ARRANGEMENT FOR EYE PRESSURE MEASUREMENTS

(71) Applicant: PHOTONO OY, Helsinki (FI)

(72) Inventors: Antti Kontiola, Helsinki (FI); Edward Häggström, Helsinki (FI); Ari Salmi, Helsinki (FI); Heikki Nieminen, Helsinki (FI)

(73) Assignee: PHOTONO OY, Helsinki (FI)

( * ) Notice: Subject to any disclaimer, the term of this patent is extended or adjusted under 35 U.S.C. 154(b) by 168 days.

(21) Appl. No.: 17/303,667

(22) Filed: Jun. 4, 2021

(65) Prior Publication Data
US 2021/0290057 A1 Sep. 23, 2021

Related U.S. Application Data

(60) Division of application No. 15/257,522, filed on Sep. 6, 2016, now Pat. No. 11,439,303, which is a
(Continued)

(30) Foreign Application Priority Data

Mar. 4, 2014 (FI) ...................................... 20145205

(51) Int. Cl.
*A61B 3/16* (2006.01)
*A61B 5/00* (2006.01)
(Continued)

(52) U.S. Cl.
CPC ............ *A61B 3/165* (2013.01); *A61B 5/0051* (2013.01); *A61B 8/10* (2013.01); *A61B 3/102* (2013.01)

(58) Field of Classification Search
CPC .......... A61B 3/165; A61B 5/0051; A61B 8/10
See application file for complete search history.

(56) References Cited

U.S. PATENT DOCUMENTS 5,251,627 A 10/1993 Morris
5,830,139 A 11/1998 Abreu
(Continued)

FOREIGN PATENT DOCUMENTS

CN 1229345 A 9/1999
CN 101083934 A 12/2007
(Continued)

OTHER PUBLICATIONS

Communication pursuant to Article 94(3) EPC issued in European Patent Application No. 15 710 219.5-1126 dated March 5. 2021.
(Continued)

*Primary Examiner* — Catherine B Kuhlman
*Assistant Examiner* — Raymond P Dulman
(74) *Attorney, Agent, or Firm* — Nixon & Vanderhye

(57) ABSTRACT

An intraocular pressure measurement arrangement is disclosed for measuring pressure of an eye of a patient. The arrangement can include at least one source for producing mechanical waves of several frequencies from a distance to the eye of the patient to generate at least one surface wave to the eye, a detector for detecting at least one surface wave from a distance from the eye to extract surface wave information, and a device for determining pressure information of the eye based on the surface wave information.

12 Claims, 3 Drawing Sheets

Figure 1:
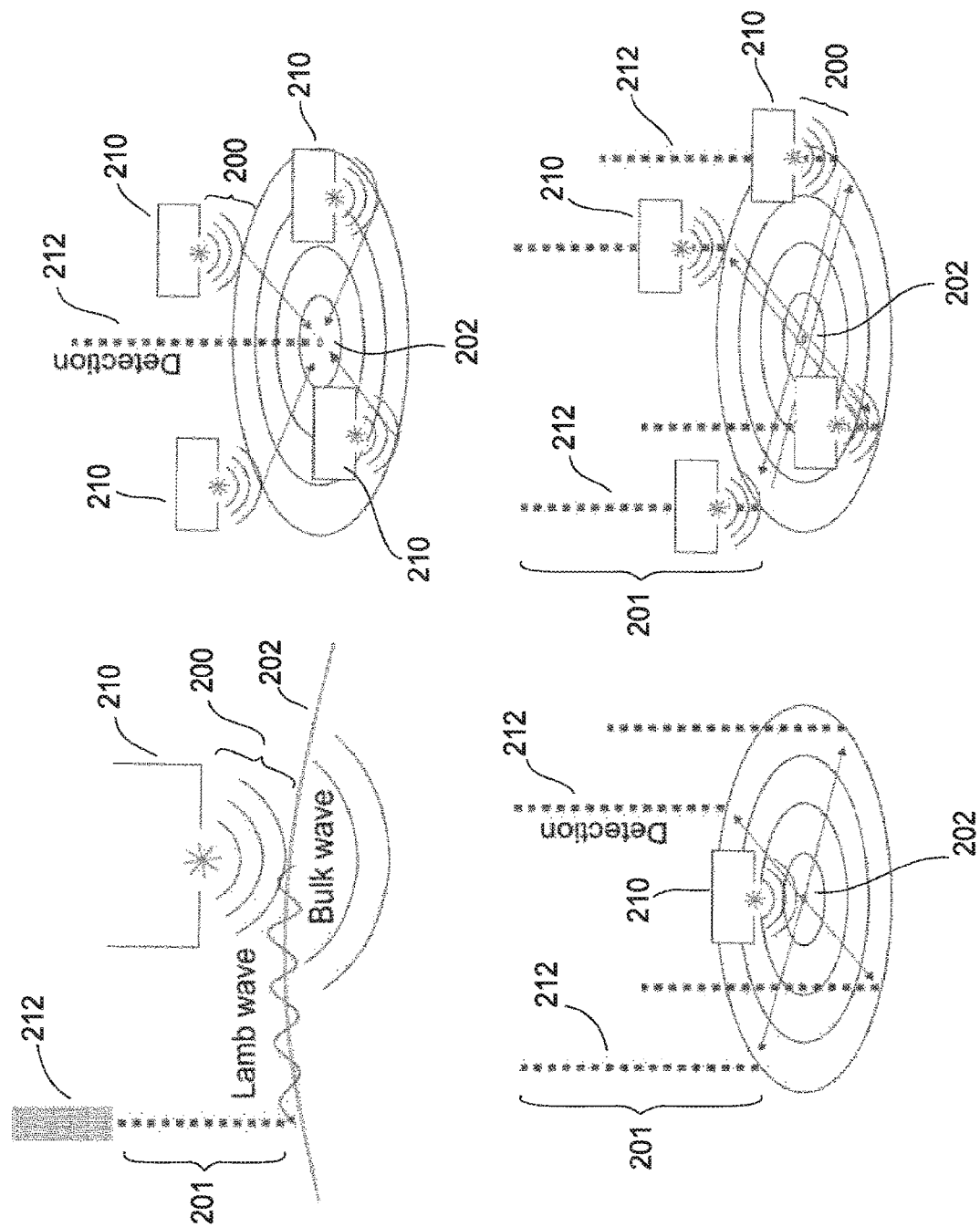

Related U.S. Application Data continuation of application No. PCT/FI2015/050133, filed on Mar. 3, 2015.

(51) Int. Cl.
*A61B 8/10* (2006.01)
*A61B 3/10* (2006.01)

(56) References Cited

U.S. PATENT DOCUMENTS

| | | | |
|---|---|---|---|
| 5,865,742 A | 2/1999 | Massie | |
| 6,030,343 A | 2/2000 | Chechersky et al. | |
| 6,159,148 A * | 12/2000 | Luce | A61B 3/165 600/405 |
| 6,694,173 B1 | 2/2004 | Bende et al. | |
| 6,976,959 B2 | 12/2005 | Fresco | |
| 8,998,810 B2 | 4/2015 | Kontiola | |
| 2002/0097374 A1 | 7/2002 | Payne et al. | |
| 2003/0078486 A1 | 4/2003 | Klein et al. | |
| 2004/0002639 A1* | 1/2004 | Luce | A61B 3/165 600/398 |
| 2004/0193033 A1 | 9/2004 | Badehi et al. | |
| 2008/0103381 A1 | 5/2008 | Kontiola | |
| 2008/0242965 A1 | 10/2008 | Norris et al. | |
| 2009/0306493 A1 | 12/2009 | Kontiola | |
| 2010/0069737 A1 | 3/2010 | Jinde et al. | |
| 2010/0168575 A1 | 7/2010 | Hashiba | |
| 2010/0249569 A1 | 9/2010 | Jinde et al. | |
| 2010/0324406 A1 | 12/2010 | Miwa | |
| 2011/0118609 A1 | 5/2011 | Goldshleger et al. | |
| 2012/0150013 A1 | 6/2012 | Peyman | |
| 2012/0277569 A1 | 11/2012 | Hogan | |
| 2013/0085370 A1 | 4/2013 | Friedman et al. | |
| 2014/0163329 A1 | 6/2014 | Brown, Jr. et al. | |
| 2016/0066786 A1 | 3/2016 | Kontiola | |
| 2016/0374554 A1 | 12/2016 | Kontiola et al. | |

FOREIGN PATENT DOCUMENTS

| | | |
|---|---|---|
| CN | 101190122 A | 6/2008 |
| DE | 19512711 C1 | 12/1996 |
| EP | 2236075 A1 | 10/2010 |
| FI | 20135401 A | 10/2014 |
| GB | 938222 A | 10/1963 |
| WO | 2014/170556 A1 | 10/2014 |

OTHER PUBLICATIONS

International Search Report (PCT/ISA/210) dated Jun. 11, 2016, by the European Patent Office as the International Searching Authority for International Application No. PCT/FI2015/050133.

Written Opinion (PCT/ISA/237) dated Jun. 11, 2016, by the European Patent Office as the International Searching Authority for International Application No. PCT/FI2015/050133.

Search Report dated Oct. 29, 2014, by the Finnish Patent Office in corresponding Finnish Patent Application No. 20145205.

Rudenko, O.V., et al., "Theoretical Foundations of Nonlinear Acoustics", Translated from Russian by Robert T. Beyer, Published by Consultants Bureau, a division of Plenum Publishing Corporation, New York, 1977 (p. 1).

International Preliminary Report on Patentability (PCT/IPEA/409) dated May 25, 2016, by the European Patent office as the International Preliminary Examining Authority for International Application No. PCT/FI2015/050133. (23 pages).

Office Action (Notification of the First Office Action) dated Oct. 25, 2017, by the Chinese Patent Office in corresponding Chinese Patent Application No. 201580011876.9, and an English Translation of the Office Action. (23 pages).

Office Action (Notification of Reasons for Refusal) dated Nov. 20, 2018, by the Japanese Patent Office in corresponding Japanese Patent Application No. 2016-197655, and an English Translation of the Office Action. (6 pages).

Office Action dated Jan. 19, 2018, by the Finnish Patent Office in corresponding Finnish Application No. 20145205. (8 pages).

Office Action dated May 28, 2018, by the Chinese Patent Office in corresponding Chinese Patent Application No. 201610875022.1 (12 pages).

Alam, S. K. et al., 'Detection of intraocular pressure change in the eye using sonoelastic Doppler ultrasound'. Ultrasound in Medicine and Biology, vol. 20, No. 8, 1994, p. 751-758, ISSN 0301-5629, DOI: 10.1016/0301-5629(94)90032-9, XP 023258908. (9 pages).

Ionophone', Wikipedia article [online], May 29, 2013 (May 29, 2013). Retrieved from the Internet: <URL: http://en.wikipedia.org/w/index.php?title=Ionophone&oldid=557426731>. [Retrieved on Oct. 14, 2014.].

Plasma speaker', Wikipedia article [online], Feb. 22, 2014 (Feb. 22, 2014). Retrieved from the Internet: <URL: http://en.wikipedia.org/w/index.php?title=Plasma_speaker&oldid=596617125>. [Retrieved on Oct. 14, 2014.] (4 pages).

Tanter, M et al., 'High-Resolution Quantitative imaging of Cornea Elasticity Using Supersonic Shear Imaging'. IEEE Transactions on Medical Imaging, vol. 28, No. 12, Nov. 25, 2009, p. 1881-1893, ISSN 0278-0062, DOI: 10.11091TMI.2009.2021471, XP011281241. (14 pages).

Zhang, X.-Y. et al., 'Preliminary Study on the Effect of Stiffness on Lamb Wave Propagation in Bovine Corneas', Proceedings of the 35th Annual Internation Conference of the IEEE EMBS, Osaka, Japan, Jul. 3-7, 2013. Piscataway, NJ: IEEE, 2013, ISSN 1557-170X, DOI: 10.1109/EMBC.2013.6609702, p. 1120-1123, XP 032488337. (5 pages).

Pinton, et al., A Heterogenous Nonlinear Attenuating Full-Wave Model of Ultrasound, Mar. 2009, IEEE Trans Ultrason Ferroelectr Freq Control, 56(3)m og 474-488 (Year: 2009).

\* cited by examiner

METHOD AND ARRANGEMENT FOR EYE PRESSURE MEASUREMENTS

CROSS-REFERENCE TO RELATED APPLICATIONS

This application is a divisional of U.S. Ser. No. 15/257,522 filed Sep. 6, 2016, which is a continuation of International Patent Application No. PCT/FI2015/050133 filed Mar. 3, 2015, which claims priority to FI Application No. 20145205 filed Mar. 4, 2014. Each of the previously noted applications is hereby incorporated by reference in their entirety.

FIELD OF THE INVENTION

Intraocular pressure (IOP) plays a major role in the pathogenesis of open angle glaucoma, a leading cause of blindness. There are about 150 million people with glaucoma globally, about half of which are unknowingly affected and without diagnosis. The prevalence of glaucoma increases with aging of the human population and it is expected that this will increase by 30% the number of glaucoma cases during the next decade. The only way to currently treat glaucoma is by lowering the intraocular pressure (IOP).

An IOP measurement is the most practical way of screening open angle glaucoma. However, screening large parts of the population is needed to find undiagnosed cases.

The other type of glaucoma is the narrow angle glaucoma that causes a sudden IOP increase that may cause blindness in a few days. Since one per mille of the population is affected with acute narrow angle closure glaucoma, it is mandatory to diagnose acute glaucoma by measuring IOP in community emergency departments of general medicine. Consequently it would be beneficial if every doctor's office would have means to measure IOP.

STATE OF THE ART

Contact methods (e.g. Goldmann tonometry, Mackay-Marg tonometry) for measuring IOP mostly require use of an anesthetic to carry out the measurement and are thus impractical e.g. for screening large human populations.

The US patent application document US 2010/0249569 A1 presents a non-contact ultrasonic tonometer for IOP measurements, which employs piezo-electric transducers to excite wave signals into the eye. The position of said transducers have to be exactly measured, which makes the IOP measurement procedure complex and slow. Also temperature variations cause error and uncertainty in the IOP measurement information together with possible errors in said position measurements. The shape of the eye also introduces bias (=error) into the measurement.

The patent document U.S. Pat. No. 6,030,343 A presents a method that is based on an airborne ultrasonic beam that is reflected from the cornea—the same beam measures and actuates the eye. The actuation is done by a narrow band ultrasonic tone burst, which deforms the cornea, and the system measures the phase shift from the deformed eye.

The prior art solutions suffer from difficulties to achieve a convenient and low-cost device for measuring IOP precisely and comfortably for the patient by non-contact measurements.

SHORT DESCRIPTION OF THE INVENTION

The object of the present invention is to achieve a contactless, fast and advanced device and method to measure IOP without need for anaesthetics. An object of the invention is to achieve an IOP reading that is both precise, i.e. unbiased and features small uncertainty in the IOP estimate. This is achieved by an IOP measurement arrangement for measuring the pressure in an eye of a patient. The arrangement comprises at least one source for producing mechanical waves of several frequencies from a distance to the eye of the patient to generate at least one surface wave to the eye, means for detecting at least one surface wave from a distance from the eye to extract surface wave information, and means to determine pressure information of the eye based on said surface wave information.

An object of the invention is also an intraocular pressure measurement method for measuring pressure in an eye of a patient. In the method is produced mechanical waves of several frequencies from a distance to the eye of the patient to generate at least one surface wave to the eye, is detected at least one surface wave from a distance from the eye to extract surface wave information, and is determined pressure information of the eye based on said surface wave information.

The invention is based on utilization of mechanical waves of several frequencies, which are sent from a distance through air to the eye of the patient to generate at least one surface wave to the eye, and on utilization of a detection, in which is detected at least one surface wave from a distance from the eye to form surface wave information for determination of pressure information of the eye.

The invention enables patient and user friendly use with no need to touch sensitive surfaces of an eye together with advanced methods to process measurement information in order to extract qualified pressure information of the eye. One benefit is that the invention can be utilized from one patient to another with less risk for contamination as contact to the eye is avoided.

SHORT DESCRIPTION OF FIGURES

FIG. 1 presents first exemplary embodiment according to the present invention.

Figure 2:
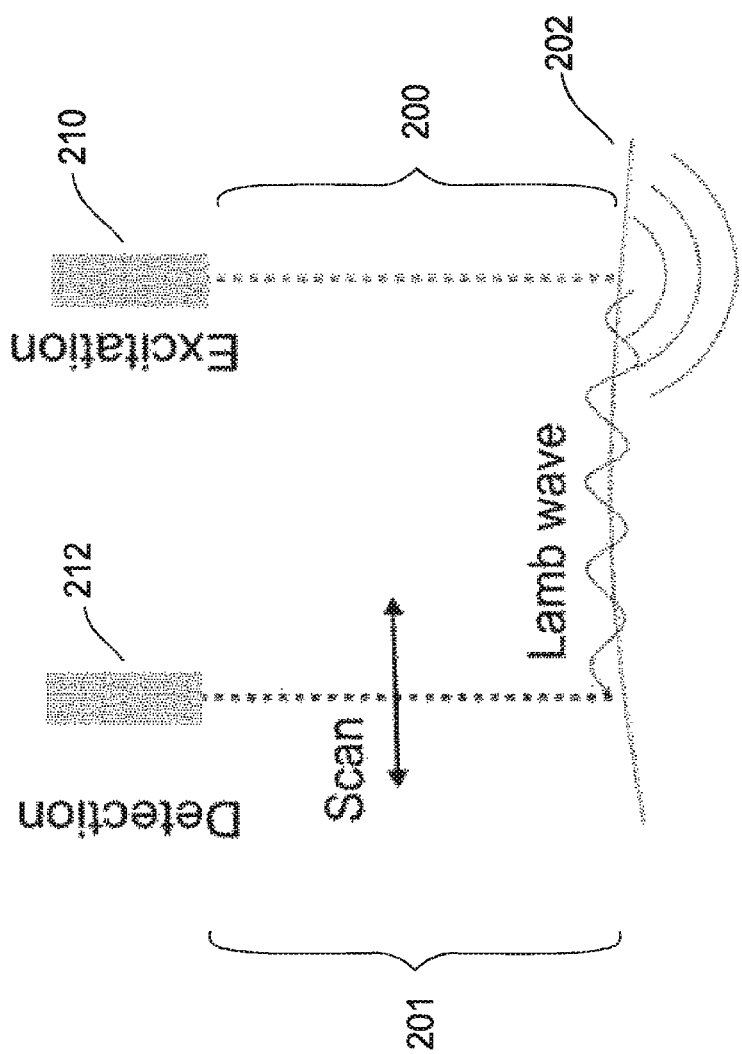

FIG. 2 presents second exemplary embodiment according to the present invention.

Figure 3:
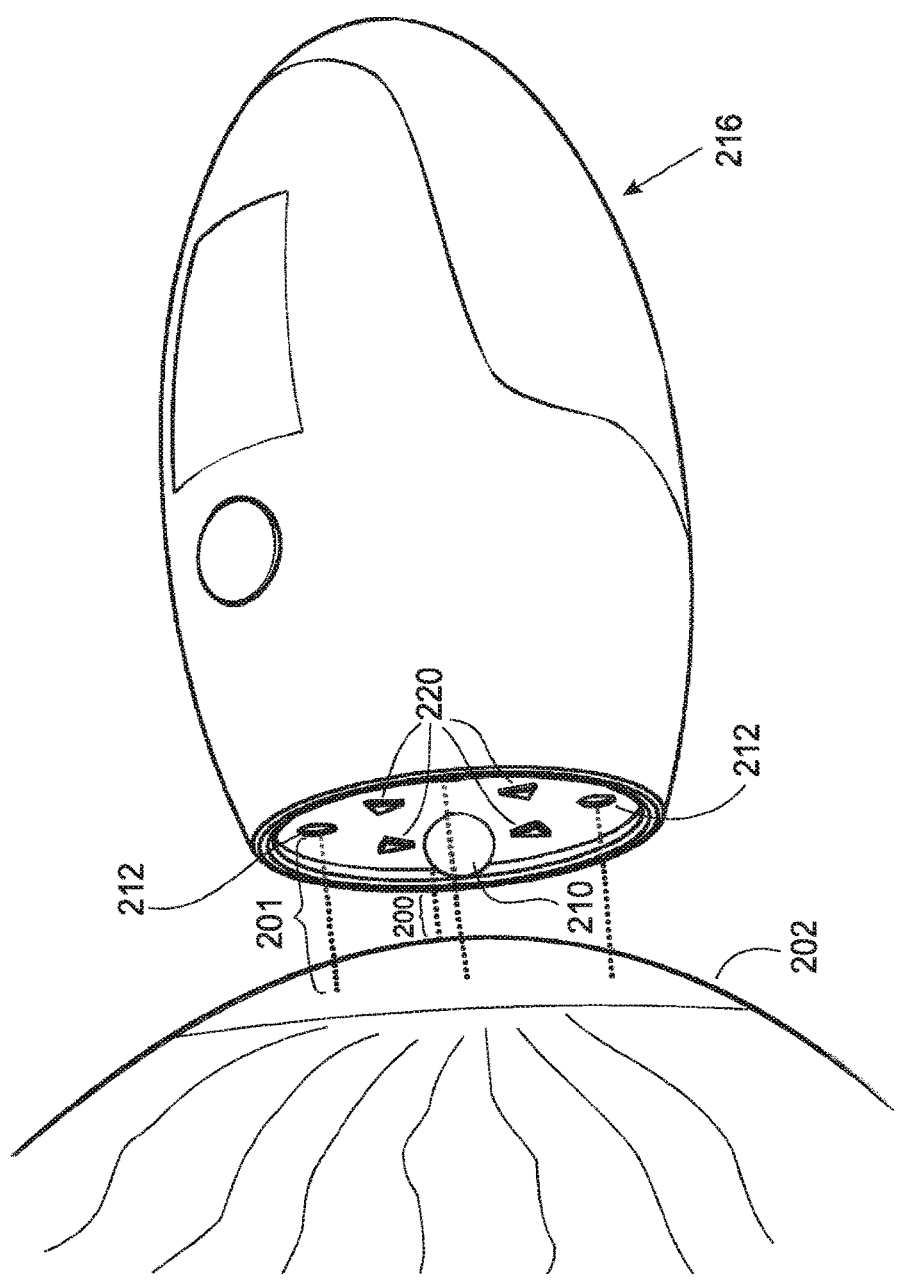

FIG. 3 presents preferred embodiment according to the present invention.

DETAILED DESCRIPTION OF THE INVENTION

Essentially, excitation and/or detection of electromagnetic waves is to be performed by means of a beam of electromagnetic waves produced e.g. by a laser, pulsed laser or a plasma source (focused laser or a spark gap), which is for example mediated via an electromagnetic waveguide (e.g. an optical fiber, collimator, lenses, masks and/or an arrangement of mirrors) and targeted onto the eye of a patient or onto a spot in the vicinity of the patient's eye. An input of the electromagnetic wave into or onto the eye is followed by electromagnetic-mechanical conversion (e.g. photo-acoustic conversion) that generates little heat and significant mechanical vibration into the eye's tissues or a plasma source that launches sound waves that impinge on the eye to create a wave in it. Correspondingly, mechanical vibrations of the eye tissue are detected (e.g. by means of optical interferometry, optical coherence tomography, laser Doppler vibrometry or ultrasound transducer). The objective is thereby to generate mechanical wave or waves (e.g. ultrasonic waves) in the eye and to detect said waves in the eye. The potential applications relate especially to determination of IOP, i.e. an eye pressure.

In the embodiments according to the present invention is presented non-contacting photoacoustic and ultrasonic intraocular pressure (IOP) measurement techniques, which may have e.g. following requirements: non-contact excitation and detection methods, which are safe for the patient, determination of essentially accurate intraocular pressure (IOP) values, possibility to follow-up of patient's IOP values, and said techniques can be used by a health care professional and/or by a patient in a convenient and ergonomic way with lowered risk for contamination from patient to patient.

There are several physical interactions that could be exploited for the IOP measurement. Next will be explained these interactions in order to evaluate their usability for a non-contact ultrasonic IOP measurement:

A) Physical systems such as the eye may vibrate at certain resonance frequencies when they are mechanically or photoacoustically disturbed. These frequencies depend on the mechanical properties of the components of the eye, and on the IOP as well as on eye size and shape as well as properties of the eye socket. Measurement of the resonance frequencies is rather easy to implement, and preliminary data can be utilized to support the viability of the resonance measurements. Guided waves, e.g. Lamb waves or quasi-Lamb waves or membrane waves that propagate on curved structures can also be used in said measurements.

B) Lamb waves are guided waves that travel along a structure. They are dispersive, i.e. the phase velocity of a Lamb wave depends on the frequency of the wave. Thus, with a single broadband excitation one can measure the dispersion relation of the waves, which is closely related to both the elasticity of the structure and stress caused by external pressure such as for example the IOP. Broadband dispersion measurements provide more accurate IOP estimates than narrow band measurements. Several independent measurements can be performed on different parts of the eye, which increases accuracy and decreases the confounding effect of the elasticity of e.g. the cornea of the eye as well as the effect of the eye socket. Preliminary data support the viability of the proposed method. Localized testing along lines can be performed, which could allow spatial averaging and could provide localized data as well as anisotropy data.

C) Bulk wave velocities, i.e. longitudinal and shear ultrasonic wave velocities, probe mechanical properties of measured materials. The propagation velocity of the longitudinal wave depends on the static pressure loading the material (e.g. liquid) in which it propagates, and said phenomena can be utilized to determine e.g. IOP. Bulk waves are simple to generate and measure, but for accurate e.g. IOP measurements other measurements than bulk wave measurements are needed, because bulk wave measurements itself are unlikely to achieve high accuracy.

D) Ultrasonic waves, both Lamb and bulk waves, loose energy as a function of propagation distance. This energy loss decreases as a function of pressure for bulk waves, but in loaded plates (e.g. the eye) due to the loading on the surface by the IOP, the effect is reversed. Quantitative measurements can be performed to calibrate the effects of external pressure on Lamb wave attenuation. Attenuation analysis is likely to be useful when combined with other properties (e.g. speed of sound, dispersion).

FIG. 1 presents a first exemplary embodiment according to the present invention, in which a spark gap 210 is placed near but not in contact with the sclera of the eye 202. The spark generates a wave that upon contacting the sclera launches two kinds of vibrations: first, elastic waves (Lamb $S_0$ and $A_0$ guided ultrasonic modes), followed by a resonant vibration of the sclera and the cornea. The vibration can be picked up e.g. with a custom made one-point interferometer 212 capable of detecting the time-of-arrival of the wave. The mode map i.e. frequency-velocity chart of Lamb waves traveling along the sclera depends on the intra-ocular pressure (IOP). Also resonant frequencies depend on IOP. This kind of embodiment is affordable and simple to produce and allows adding detectors to increase the measurement accuracy. Also a high signal-to-noise ratio can be achieved by this kind of implementation.

The spark gap 210 produces a bright flash of light that might harm the eye 202. This can be avoided with a thin black membrane not in contact with the eye. The membrane passes the acoustic pressure wave and blocks the light from reaching the eye. The weak mechanical and/or acoustic nonlinear wave, which is e.g. transient, broadband or shock wave, generated by the spark can be audible and does not induce tissue-breaking stress. The intensity of the emitted wave can be controlled to ensure that there is no risk to the hearing. Also the detectors can use very low power lasers (even Class 1) in order to introduce no safety risks to the eye.

The first exemplary embodiment can be further improved by incorporating a custom made one-point interferometer capable of measuring vibration as a function of time. This increases costs, but allows simultaneous measurement of both the resonance and the traveling Lamb waves, thus yielding more accurate IOP measurement information.

FIG. 2 presents a second exemplary embodiment according to the present invention, in which is utilized a pulsed e.g. KrF excimer laser 210 (e.g. 248 nm) to excite mechanical wave(s) and e.g. a laser Doppler vibrometer (LDV) as detecting means 212. The excimer laser can be focused on either the sclera or the cornea of the eye 202 or close to them both, launching Lamb waves to the eye which are detected by a detection system 212, e.g. the LDV. Several parameters can concurrently be detected and correlated and calibrated to IOP: speed of sound, attenuation, vibration spectrum of the received signal, detected resonance frequency, etc.

UV wavelengths (or 1300-1550 nm IR (infrared)) absorb strongly into the cornea, and are thus unlikely to traverse the sclera. Interferometers use generally a Class 1 beam, which is safe to the eye. The generated Lamb waves do not cause discomfort or damage. E.g. the 248 nm wavelength absorbs extremely well into both the cornea and the sclera, thus not damaging eye structures beneath them. Benefits of the second embodiment are also low intensity values which causes no discomfort to the patient and high absorption coefficient which improves signal to noise ratio and hence both precision and accuracy of the IOP estimate. Also e.g. phase-delayed laser diodes can be used to shape the spectrum of the transmit signal to increase the signal to noise ratio in the four modes in the mode map that is analyzed.

In the first and second exemplary embodiment according to the present invention is accomplished photoacoustic IOP measurements based on Lamb wave velocity dispersion and resonant frequencies of the eye/sclera. A bi-modality embodiment, i.e. concurrent use of Lamb wave measurements and resonance measurements can be accomplished e.g. by four detection points to pick up the wave excited in the middle to allow four simultaneous and independent measurements. This provides precision. The sensor 212 can also comprise e.g. ultrasonic transducers coupled to air which to serve as distance and tilt measurement devices. An IOP measurement device (e.g. FIG. 3) according to the present can comprise e.g. a spark gap 210 in the middle of the device, detection means to pick up the excited waves from four points around an excitation point on the surface of the eye 210 and a built-in ultrasonic sensor 220 detecting the distance of the device from the eye and the tilt of the device. The device can further comprise direction lights or a display unit to indicate into which direction it should be tilted. This makes it more operator friendly.

FIG. 3 presents a first preferred intraocular pressure (IOP) measurement arrangement according to the present invention for measuring the pressure in an eye 202 of a patient. The arrangement comprises at least one source 210 for producing mechanical waves of several frequencies from a distance 200 through air to the eye 202 of the patient. Said waves generate at least one surface wave to the eye, and more specifically to a certain surface area of the eye and near the surface area of the eye. The invention can enable probing a certain site of the eye if one wants to and even a certain direction along the eye ball. The surface waves preferably comprise modes, e.g. Lamb $S_0$ and $A_0$ guided ultrasonic modes, and also resonant vibrations that are generated to the eye. The source 210 is preferably a spark gap 210 that generates by at least one spark an acoustic nonlinear wave, e.g. shock wave that couples to the eye 202 through the air and generates e.g. both Lamb waves and resonant vibrations to the surface of the eye 202 and into the eye 202. The surface wave or waves are detected by means 212 for detecting from a distance 201 from the eye 202 to form surface wave information. Preferably also resonant vibrations are detected by means 212 for detecting from a distance 201 from the eye 202 to form resonance information. Detection of the propagating waves can be based on e.g. the time-of-arrival of the first arriving signal (FAS), whereas the detection of the resonances can be based on e.g. the Fourier transform of the measured signal.

As is apparent to a person skilled in the art the mechanical nonlinear wave can also be generated by a mechanical impact of a combination of two hard surfaces or corners or edges (210) as the source (210) for producing nonlinear acoustic or mechanical waves, e.g. shock waves, of several frequencies from a distance (200) said waves coupling to the eye (202) of the patient. For example it is commonly known that a hammer strike can produce nonlinear wide spectrum acoustic signal including ultrasonic frequencies.

The distance 200 or the distance 201, or both of them, can be optimized by means 220 for controlling distance. The means 220 can be implemented e.g. by ultrasonic transducers coupled to air for distance or tilt measurements and aiding the operator to position the device. Also accelerometers or gyroscopes can be used to detect the best position and time moment for the measurements. The means 220 for controlling and setting an optimized distance 200, 201 from the source 210 and from the means 212 to the surface of the eye 202 can also be implemented by an embodiment, in which the means 220 comprises at least one laser emitting visible light, and at least two e.g. light guides having first ends and second ends, said first ends connected to said laser for receiving said visible light. The means 220 can also comprise positioning means for moving the source 210 for producing mechanical waves or the detecting means 212 into different points e.g. along a predetermined path. Each of said second ends provides a light beam, and these light beams are directed towards a surface of the eye 202 with an angle of convergence K. The light beams are adjusted to intersect in a predetermined focus point, which is visible on the surface of the eye and which indicates the proper position and distance 200, 201 from the source 210 and from the means 212 to the surface of the eye 202.

The arrangement in FIG. 3 also comprises means 216 for determining pressure information of the eye based on the surface wave information and preferably based also on the resonance information. The means 216 can be implemented by e.g. a processor unit in an IOP measurement device or by a separate computer unit to which measurement information is sent from the IOP measurement unit via a wireless or wired connection link. The means 212 for detecting can be implemented for example by means of optical interferometry, i.e. by an optical interferometer, by means of optical coherence tomography, i.e. by an optical coherence tomography device, or by means of laser Doppler vibrometry, i.e. by a laser Doppler vibrometer, or by ultrasonic measurements using at least one ultrasonic transducer, or with a combination of the different techniques. In the first preferred arrangement the means 212 for detecting at least one surface wave comprises at least one interferometer 212, which can measure the vibrations as a function of time, and which allows simultaneous measurement of both the resonance vibrations and of the surface waves, i.e. the Lamb waves, thus yielding a precise and accurate estimate of the pressure of the eye 202. The invention can permit use of one cheap single point interferometer or more of them to detect time of arrival.

There can be either at least two wave sources 210 or detecting means 212, or at least two of both, to improve measurement accuracy in forming the surface wave information and the resonance information. In the preferred arrangement of FIG. 3 the detecting means 212 are in three different detection locations in order to improve measurement accuracy and precision and to obtain higher signal-to-noise ratio.

Heartbeat, eye blinking, and respiration cause temporal fluctuations in intraocular pressure. Of these, the heartbeat causes relatively constant pulsatile peaks in IOP, normally between 2-3 mmHg. This difference is called ocular pulse amplitude. This amplitude depends on heart rate and axial length and there is a positive linear correlation between ocular pulse amplitude and IOP. High IOP causes high ocular pulse amplitude. Several other parameters, including ocular rigidity affects the magnitude of the ocular pulse amplitude. These pressure peaks cause vibrations and waves along the eyeball (sclera and cornea) and also internally (e.g. iris), and said waves and vibrations can be detected e.g. optically. The device according to the present invention can be used to measure, monitor, and analyze these heart beat induced changes in said vibrations and waves to estimate IOP also without external stimulus.

Embodiments according to the present invention can improve comfort, accuracy, and precision of the IOP measurement by utilizing at least one of the following features: 1) employing non-contacting measurement (comfort), 2) employing a localized and directional measurement (reduces eye shape-induced bias (error) to improve accuracy), 3) employing a slow wave form (symmetric & asymmetric Lamb waves, which reduces the confidence limits of the sound velocity estimate=improves the precision of the elasticity estimate=improves the precision of the IOP estimate, 4) employing a broadband signal which allows mapping several propagating modes to gain precision in the sound velocity estimate (improves precision and potentially accuracy of the tester) 5) employing a geometric transmit and receive array or phased array (improved SNR which reduces the confidence limits of the sound velocity estimate due to larger signals and due to ability to fit the estimate with a regression line, this improves precision), 6) the array approach also allows tuning the modes to be employed for improved SNR and consequently precision and accuracy of the tester/test, 7) employing both the travelling wave approach described above and the resonance concept known to the state of the art. Since these measurements are independent of each other a more sensitive and robust tester follows (it should improve both precision and accuracy). The measurement can be generalized to other physical parameters such as sound attenuation (absorption, scattering) and sound velocity dispersion.

In one embodiment according to the present invention can be utilized patient heartbeat or breathing or both of them as a source for producing surface waves of several frequencies from a distance 200 to the eye 202 of the patient. In another embodiment according to the present invention can be utilized means 210 to generate tiny plasma burst as the source 210 for producing acoustic waves of several frequencies from a distance 200 to the eye 202 of the patient. Said generation can be made by sparking or by focusing a laser ray to one point on the surface of the eye or close to the surface of the eye. In one further embodiment according to the present invention can be utilized means 210 to generate chemical reaction as the source 210 for producing acoustic waves of several frequencies from a distance 200 to the eye 202 of the patient.

In embodiments according to the present invention can be utilized mode tuning by phase delayed excitation in source 210 for producing mechanical waves of several frequencies from a distance 200 through air to the eye 202 of the patient. An improved signal to noise ratio (SNR) and improved time of flight (TOF) estimate can be achieved by mode tuning performed on the basis of phase delayed excitation. Precision and accuracy of IOP measurements according to the present invention can thus be increased.

Also, in an embodiment according to the present invention a photoacoustic laser-based excitation can be performed by having a ring shaped form to the surface of the eye or close to that surface in order to amplify the surface wave in the middle of the ring shape. This enables easier and more accurate detection to be performed by the detection means. It also permits a cheaper receiver to be used. The user can combine the use of a shaped, i.e. circle or line or crescent source with the phased array concept having many dots, lines or crescents for improved precision and accuracy in the IOP measurement.

On the basis of the present invention can be implemented an ideal tonometer capable of measuring intraocular pressure with fast comfortable measurements without anesthetic and disposable waste operated also by an unskilled operator.

Although the invention has been presented in reference to the attached figures and specification, the invention is by no means limited to those, as the invention is subject to variations within the scope allowed for by the claims.

The invention claimed is:

1. An intraocular pressure measurement method for measuring pressure of an eye of a patient, comprising:
producing a nonlinear acoustic or a nonlinear mechanical wave from a distance coupling through air to an eye of a patient to generate at least one surface wave to the eye;
detecting at least one surface wave from a distance from the eye to extract surface wave information; and
determining pressure information of the eye based on said surface wave information, where the nonlinear acoustic or nonlinear mechanical wave is a transient or shock wave.

2. An intraocular pressure measurement method according to claim 1, wherein the surface wave is a membrane wave.

3. An intraocular pressure measurement method according to claim 1, wherein the method comprises:
generating at least one surface wave and resonant vibrations to the eye;
detecting the at least one surface wave and the resonant vibrations from a distance from the eye to form surface wave information and resonance information; and
determining pressure information of the eye based on the surface wave information and the resonance information.

4. An intraocular pressure measurement method according to claim 1, wherein the method comprises: detecting at least one surface wave by at least one interferometer.

5. An intraocular pressure measurement method according to claim 1, wherein the method comprises: sparking mechanical waves of several frequencies from a distance to the eye of the patient.

6. An intraocular pressure measurement method according to claim 1, wherein the method comprises: detecting at least in two different detection locations in order to improve measurement accuracy and to obtain higher signal-to-noise ratio.

7. An intraocular pressure measurement method according to claim 1, wherein the method comprises: controlling at least one distance of an excitation distance and a detection distance.

8. An intraocular pressure measurement method according to claim 1, wherein the method comprises: detecting by at least one of optical interferometry, optical coherence tomography, laser Doppler vibrometry and ultrasonic measurements at least one surface wave.

9. An intraocular pressure measurement method according to claim 1, wherein the method comprises: detecting resonance vibrations based on detection of a first arriving signal (FAS).

10. An intraocular pressure measurement method according to claim 1, wherein the method comprises: producing surface waves of several frequencies from a distance to the eye of the patient by utilizing at least one of a patient heartbeat and breathing.

11. An intraocular pressure measurement method according to claim 1, wherein the method comprises: generating plasma burst to produce mechanical waves of several frequencies from a distance to the eye of the patient.

12. An intraocular pressure measurement method according to claim 1, wherein the method comprises: generating a chemical reaction to produce mechanical waves of several frequencies from a distance to the eye of the patient.

* * * * *